United States Patent [19]

Arraudeau et al.

[11] Patent Number: 4,871,536
[45] Date of Patent: Oct. 3, 1989

[54] COMPOSITION BASED ON CATIONIC POLYMERS, ANIONIC POLYMERS AND WAXES FOR USE IN COSMETICS

[75] Inventors: Jean-Pierre Arraudeau; Jeanne Patraud, both of Paris; Louis Le Gall, Bures-sur-Yvette, all of France

[73] Assignee: L'Oreal, France

[21] Appl. No.: 225,583

[22] Filed: Jul. 28, 1988

Related U.S. Application Data

[63] Continuation of Ser. No. 834,120, Feb. 26, 1986, abandoned, which is a continuation of Ser. No. 505,265, Jun. 17, 1983, abandoned.

[30] Foreign Application Priority Data

Jun. 17, 1983 [LU] Luxembourg ............................ 84210

[51] Int. Cl.[4] ..................... A61K 7/021; A61K 7/031; A61K 7/032; A61K 7/42
[52] U.S. Cl. ......................................... 424/59; 424/60; 424/63; 424/64; 424/78; 514/844; 514/845; 514/873; 514/938
[58] Field of Search ...................... 424/63, 64, 78, 81

[56] References Cited

U.S. PATENT DOCUMENTS

4,402,977 9/1983 Grollier et al. ........................ 424/70

FOREIGN PATENT DOCUMENTS

| 1324745 | 7/1973 | United Kingdom . |
| 1560428 | 2/1980 | United Kingdom . |
| 1569500 | 6/1980 | United Kingdom . |
| 2063671 | 6/1981 | United Kingdom ................... 424/71 |
| 1603321 | 11/1981 | United Kingdom . |
| 1603322 | 11/1981 | United Kingdom . |
| 1603323 | 11/1981 | United Kingdom . |
| 1603324 | 11/1981 | United Kingdom . |
| 2107186 | 4/1983 | United Kingdom . |

*Primary Examiner*—Dale R. Ore
*Attorney, Agent, or Firm*—Fleit, Jacobson, Cohn, Price, Holman & Stern

[57] ABSTRACT

The invention relates to cosmetic compositions comprising at least one wax having a melting point of 60° to 110° C., at least one cationic polymer having a molecular weight of between 1,000 and 3,000,000, at least one anionic polymer and ingredients normally used in cosmetics.

14 Claims, No Drawings

COMPOSITION BASED ON CATIONIC POLYMERS, ANIONIC POLYMERS AND WAXES FOR USE IN COSMETICS

This application is a continuation of application Ser. No. 834,120, filed Feb. 26, 1986, now abandoned, which is a continuation of application Ser. No. 505,265, filed June 17, 1983, now abandoned.

The present invention relates to the combined use of cationic polymers, anionic polymers and waxes in cosmetic compositions.

It is well known to use waxes in make-up compositions.

One of the main problems encountered in this type of product, however, relates to the adhesion and the persistence of the make-up on the skin.

Another problem relates to good distribution of the wax and the stability of the composition with time.

It is also desirable, moreover, to obtain better uniformity of the make-up and to prevent the "film" from breaking. In one particular application involving mascaras, ways are being sought which would make it possible to improve the lengthening of the eyelashes.

Finally, cosmetic compositions, in particular make-up compositions, generally contain pigments, and attempts are being made to improve the distribution of the pigments in the composition in order to give a more uniform coloration of the composition and the film.

We have discovered, according to the present invention, that, by using at least one cationic polymer and at least one anionic polymer in combination with the waxes, it is possible to prepare a cosmetic composition having improved stability. Furthermore, it has been found that it is possible, using this composition, to form films which, when applied to a substrate, make it possible to extend the surface of this substrate.

These results have been obtained, in particular, for a special class of waxes which are vegatable, mineral, animal or synthetic waxes having a melting point of 60° to 110° C. and a needle penetration at 25° C. of 3 to 40 according to ASTM Method D 5.

Furthermore, it has been found that the use of a cationic polymer and an anionic polymer with the waxes makes it possible to obtain better distribution of the pigments in these compositions.

The present invention therefore provides a composition based on cationic polymers, anionic polymers and waxes having a melting point of 60° to 110° C., which are intended for use in cosmetics, as well as a process of cosmetic treatment, in particular of the skin, which uses this combination.

The compositions, according to the invention, intended for use in cosmetics are essentially characterised in that they contain at least one wax having a melting point of 60° to 110° C. and, preferably, a needle penetration at 25° C. of 3 to 40, at least one cationic polymer having a molecular weight of 1,000 to 3,000,000 and at least one anionic polymer, in the presence of a suitable cosmetic excipient.

The amount of cationic polymer is suitably 0.1 to 10%, and preferably 0.1 to 5%, by weight relative to the total weight of the composition; the concentration of anionic polymer is suitably 0.1 to 10%, and preferably 0.1 to 5%, by weight relative to the total weight of the composition, these percentages being expressed as percentages of active ingredients.

The amount of wax is suitably 2 to 40% by weight relative to the total weight of the composition, and preferably from 5 to 40%.

The waxes used in the present invention are chosen from animal waxes, vegetable waxes, mineral waxes and synthetic waxes having melting points of 60° to 110° C. and preferably having needle penetrations at 25° C. of 3 to 40. These waxes are insoluble in water and have a crystalline structure.

The waxes which can be used more particularly according to the invention are, in the case of the animal waxes, beeswaxes and Chinese waxes, and in the case of the vegetable waxes, carnauba wax, candelilla wax, ouricury wax, cork fibre wax, sugarcane wax or Japan wax.

In the case of the mineral waxes, there may be mentioned, in particular, paraffins, microcrystalline waxes, ozokerites, montan waxes and also compositions based on these waxes and on products such as ceresine.

In the case of the synthetic waxes, there may be mentioned polyethylene waxes, the waxes obtained by Fischer-Tropsch synthesis and waxy copolymers as well as their esters.

These waxes are well known in the state of the art. According to the invention, the waxes which can be used should preferably be solid and rigid at a temperature below 50° C.

The cationic polymers used according to the invention are, in particular, polymers of the polyamine, polyaminopolyamide or poly-(quaternary ammonium) type, the amine or ammonium group forming part of the polymer chain or being joined thereto, and have molecular weights of 1,000 to 3,000,000.

Such polymers are described, in particular, in French Patents and French Patent Applications Nos. 2,077,143, 1,492,597, 2,162,025, 2,280,361, 2,252,840, 2,368,508, 1,538,363, 2,080,759, 2,190,406, 2,320,330, 2,270,846, 2,316,271, 2,336,434, 2,189,434 and 2,413,907, and U.S. Pat. Nos. 3,589,978, 4,031,307, 3,227,615, 2,961,347, 2,273,780, 2,375,853, 2,388,614, 2,454,547, 3,260,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Polymers of this type which can be used according to the invention are, in particular:

(1°) Vinylpyrrolidone/dialkylaminoalkyl acrylate or methyacrylate copolymers (quaternised or unquaternised) such as those sold under the name Gafquat by Gaf Corp., for example "copolymer 845" and Gafquat 734 or 755", described in greater detail in particular in French Pat. No. 2,077,143 and French Patent Application 2,393,573.

(2°) Cellulose ether derivatives containing quaternary ammonium groups, such as those described in French Pat. No. 1,492,597 and in particular the polymers sold under the name JR, such as JR 125, JR 400 and JR 30 M, and under the name LR, such as LR 400 and LR 30 M, by the Union Carbide Corp., and cationic cellulose derivatives such as CELQUAT L 200 and CELQUAT H 100 sold by National Starch.

(3°) Cationic polysaccharides such as those described in U.S. Pat. Nos. 3,589,978 and 4,031,307, and in particular Jaguar C. 13 S sold by Meyhall.

(4°) Cationic polymers chosen from the group comprising:
(a) polymers containing units of the formula:
—A—Z—A—Z— (I) in which A denotes a radical containing two amino groups, preferably

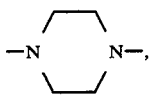

and Z denotes the symbol B or B'; B and B', which are identical or different, denote a divalent radical which is a straight-chain or branched-chain alkylene radical which contains up to 7 consecutive carbon atoms in the main chain, which is unsubstituted or substituted by one or more hydroxyl groups and which can also contain oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium, amine, alkylamine, alkenylamine, benzylamine, amine oxide, quaternary ammonium, amide, imide, alcohol, ester and/or urethane groups; these polymers and the process for their preparation are described in French Pat. No. 2,162,025 or U.S. Pat. No. 3,917,817.

(b) polymers containing units of the formula: $-A-Z_1-A-Z_1-$ (II), in which A denotes a radical containing two amino groups, preferably

and $Z_1$ denotes the symbol $B_1$ or $B'_1$ and denotes the symbol $B'_1$ at least once; $B_1$ denotes a divalent radical which is a straight-chain or branched-chain alkylene or hydroxyalkylene radical having up to 7 consecutive carbon atoms in the main chain, and $B'_1$ is a divalent radical which is a straight-chain or branched-chain alkylene radical which has up to 7 consecutive carbon atoms in the main chain, which is unsubstituted or substituted by one or more hydroxyl radicals and which is interrupted by one or more chain nitrogen atoms, the nitrogen atom being substituted by an alkyl radical which is optionally interrupted by a chain oxygen atom and which contains one or more hydroxyl groups; these polymers and the process for their preparation are described in French Pat. No. 2,280,361 or U.S. Pat. No. 4,013,787; and (c) the quaternary ammonium salts and the oxidation products of the polymers of the formulae indicated above under (a) and (b).

(5°) Optionally alkylated, crosslinked polyaminopolyamides chosen from at least one water-soluble crosslinked polymer obtained by crosslinking a polyaminopolyamide (A) prepared by the polycondensation of an acid compound with a polyamine. The acid compound is chosen from amongst: (i) organic dicarboxylic acids, (ii) aliphatic monocarboxylic and dicarboxylic acids with a double bond, (iii) the esters of the abovementioned acids, preferably the esters with lower alkanols having from 1 to 6 carbon atoms, and (iv) mixtures of these compounds. The polyamine is a bis-primary, mono-secondary or bis-secondary polyalkylene-polyamine. Up to 40 mol% of this polyamine can be replaced by a bis-primary diamine, preferably ethylenediamine, or by a bis-secondary diamine, preferably piperazine, and up to 20 mol% can be replaced by hexamethylenediamine. The crosslinking is carried out by means of a crosslinking agent (B) chosen from epihalogenohydrins, diepoxides, dianhydrides, unsaturated anhydrides and bis-unsaturated derivatives. The crosslinking is characterised in that it is carried out by means of 0.025 to 0.35 mol of crosslinking agent per amine group of the polyaminopolyamide (A), generally by means of 0.025 to about 0.2 and in particular by means of 0.025 to about 0.1 mol of crosslinking agent per amine group of the polyaminopolyamide (A). These polymers and the process for their preparation are described in greater detail in French Pat. No. 2,252,840 or U.S. Pat. No. 4,172,887.

These crosslinked polymers are soluble in water to the extent of at least 10% without forming a gel, and the viscosity of a 10% strength solution in water at 25° C. is at least 3 centipoises and usually 3 to 200 centipoises.

The polyaminopolyamides (A) themselves can also be used according to the invention.

(6°) Water-soluble crosslinked polyaminopolyamides obtained by crosslinking a polyaminopolyamide (A) (described above) by means of a crosslinking agent chosen from:

(I) compounds from the group comprising (1) bis-halogenhydrins, (2) bis-azetidinium compounds, (3) bis-halogenacyldiamines and (4) bis-(alkyl halides);

(II) oligomers obtained by reacting a compound (a) chosen from (1) bis-halogenohydrins, (2) bis-azetidinium compounds, (3) bis-halogenoacyldiamines, (4) bis-(alkyl halides), (5) epihalogenhydrins, (6) diepoxides and (7) bis-unsaturated derivatives, with a compound (b) which is a difunctional compound reactive towards the compound (a); and (III) the quaternisation product of a compound chosen from the compounds (a) mentioned above and the oligomers (II) and containing one or more tertiary amine groups which can be totally or partially alkylated, with an alkylating agent (c) preferably chosen from methyl or ethyl chlorides, bromides, iodides, sulphates, mesylates and tosylates, benzyl chloride or bromide, ethylene oxide, propylene oxide and glycidol. The crosslinking is carried out by means of 0.025 to 0.35 mol, in particular by means of 0.025 to 0.2 mol and more particularly by means of 0.025 to 0.1 mol of crosslinking agent per amine group of the polyaminopolyamide.

These crosslinking agents and these polymers, and also the process for their preparation, are described in French Patent Application No. 2,368,508 or in U.S. Pat. No. 4,189,468.

(7°) Polyaminopolyamide derivatives resulting from the condensation of polyalkylene-polyamines with polycarboxylic acids, followed by alkylation with difunctional agents. Examples which may be mentioned are adipic acid/dialkylaminohydroxyalkyl-dialkylene-triamine polymers in which the alkyl radical contains from 1 to 4 carbon atoms and preferably denotes methyl, ethyl or propyl, which are described in French Pat. No. 1,583,363.

Amongst these derivatives, there may be mentioned the adipic acid/dimethylaminohydroxypropyl-diethylenetriamine polymers sold under the name Cartaré tine F, F4 or F8 by SANDOZ.

(8°) Polymers obtained by reacting a polyalkylene-polyamine containing two primary amine groups and at least one secondary amine group with a dicarboxylic acid chosen from amongst diglycolic acid and saturated aliphatic dicarboxylic acids having from 3 to 8 carbon atoms, the molar ratio of the polyalkylene-polyamine to the dicarboxylic acid being from 0.8:1 to 1.4:1, and the resulting polyaminopolyamide being reacted with epichlorohydrin in a molar ratio of epichlorohydrin to the secondary amine groups of the polyaminopolyamide of 0.5:1 to 1.8:1; these polymers are mentioned in U.S. Pat. Nos. 3,227,615 and 2,961,347.

The polymers of this type are, in particular, that sold under the name HERCOSETT 57 by Hercules Incorporated, which has a viscosity at 25° C. of 30 cps in 10% strength aqueous solution, and that sold under the name PD 170 or DELSETTE 101 by Hercules in the case of the adipic acid/epoxypropyl-diethylenetriamine copolymer.

(9°) Cyclic polymers having a molecular weight of 20,000 to 3,000,000, such as homopolymers containing, as the main constituent of the chain, units corresponding to the formula (III) or (III'):

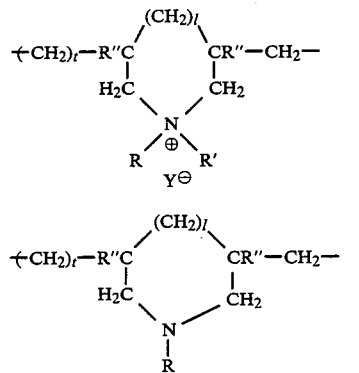

in which l and t are equal to 0 or 1 and the sum l+t=1, R" denotes hydrogen or methyl, R and R' independently of one another denote an alkyl group having from 1 to 22 carbon atoms, a hydroxyalkyl group in which the alkyl group preferably has 1 to 5 carbon atoms, or a lower amidoalkyl group, or R and R' denote, together with the nitrogen atom to which they are attached, a heterocyclic group such as piperidinyl or morpholinyl, and also the copolymers containing units of the formula III or III' and units derived from acrylamide or from diacetone-acrylamide, and $Y^\ominus$ is an anion such as bromide, chloride, acetate, borate, citrate, tartrate, bisulphate, bisulphite, sulphate or phosphate.

Amongst the quaternary ammonium polymers of the type defined above, there may be mentioned the dimethyldiallylammonium chloride homopolymer sold under the name MERQUAT 100, which has a molecular weight of less than 100,000, and the dimethyldiallylammonium chloride/acrylamide copolymer having a molecular weight of more than 500,000, which is sold under the name MERQUAT 550 by MERCK.

These polymers are described in French Pat. No. 2,080,759 and its patent of addition No. 2,190,406.

(10°) Poly-(quaternary ammonium) compounds containing units of the formula:

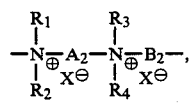  (IV)

in which $R_1$ and $R_2$, and $R_3$ and $R_4$, which are identical or different, represent aliphatic, alicyclic or arylaliphatic radicals containing at most 20 carbon atoms, or lower hydroxyaliphatic radicals, or alternatively $R_1$ and $R_2$, and $R_3$ and $R_4$, together or separately form, with the nitrogen atoms to which they are attached, heterocyclic rings optionally containing a second heteroatom other than nitrogen, or alternatively $R_1$, $R_2$, $R_3$ and $R_4$ represent a group:

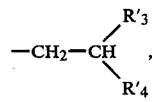

in which $R'_3$ denotes hydrogen or lower alkyl and $R'_4$ denotes one of the following groups:

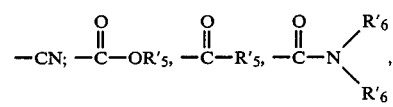

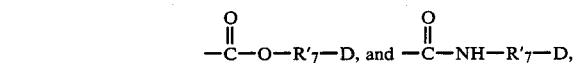

$R'_5$ denoting a lower alkyl group, $R'_6$ denoting hydrogen or a lower alkyl group, $R'_7$ denoting alkylene and D denoting a quaternary ammonium group, $A_2$ and $B_2$ represent aliphatic groups containing from 2 to 20 carbon atoms, which can be linear or branched and saturated or unsaturated and which can contain, inserted in the main chain, one or more aromatic rings, such as the group:

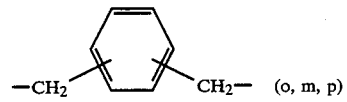

or one or more groups:

$-(CH_2)_n-Y_1-(CH_2)_n-$, $Y_1$ denoting O, S, SO, $SO_2$,

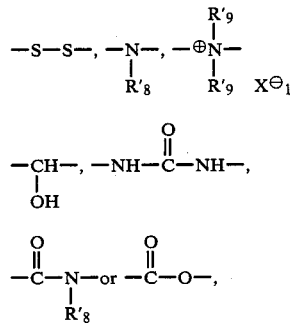

with $X_1$ denoting an anion derived from a mineral or organic acid, n being 2 or 3, $R'_8$ denoting hydrogen or a lower alkyl group and $R'_9$ denoting lower alkyl, or alternatively $A_2$ and $R_1$ and $R_3$ together form a piperazine ring with the two nitrogen atoms to which they are attached; moreover, if $A_2$ denotes a linear or branched, saturated or unsaturated aliphatic or hydroxyaliphatic radical, $B_2$ can also denote a group:

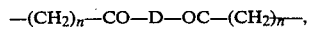

in which D denotes:
(a) a glycol radical of the formula —O—Z—O—, in which Z denotes a linear or branched hydrocarbon radical or a group corresponding to the formulae:

[CH$_2$—CH$_2$—O]$_x$ CH$_2$—CH$_2$— or $$+CH_2-\underset{CH_3}{\underset{|}{CH}}-O+_y CH_2-\underset{CH_3}{\underset{|}{CH}}-,$$

in which x and y independently denote an integer from 1 to 4, (representing a definite degree of polymerisation, or any integer or decimal number from 1 to 4, representing a mean degree of polymerisation;
(b) a bis-secondary diamine radical such as a piperazine derivative of the formula:

$$-N\diagup\overline{\phantom{xx}}\diagdown N-;$$

(c) a bis-primary diamine radical of the formula:

—NH—Y—NH—, in which Y denotes a linear or branched hydrocarbon radical or the divalent radical

—CH$_2$—CH$_2$—S—S—CH$_2$—CH$_2$—;

or
(d) a ureylene group of the formula —NH—CO—NH—; and X$^-$ is an anion such as chloride or bromide.

These polymers generally have a molecular weight of 1,000 to 100,000.

Polymers of this type are described, in particular, in French Pat. Nos. 2,320,330, 2,270,846 and 2,316,271, French Application Nos. 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11°) Homopolymers or copolymers derived from acrylic or methacrylic acid and containing the unit:

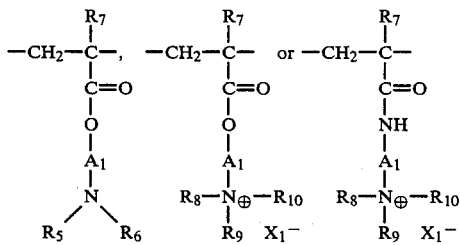

in which R$_7$ is H or CH$_3$, A$_1$ is a linear or branched alkyl group having 1 to 6 carbon atoms or a hydroxyalkyl group having 1 to 4 carbon atoms, R$_8$, R$_9$ and R$_{10}$, which are identical or different, represent an alkyl group having from 1 to 18 carbon atoms or a benzyl group, R$_5$ and R$_6$ represent hydrogen or an alkyl group having from 1 to 6 carbon atoms, and X$_1$ denotes a methosulphate anion or a halide such as chloride or bromide.

The comonomer or comonomers which can be used is typically: acrylamide, methacrylamide, diacetoneacrylamide, acrylamide or methacrylamide substituted on the nitrogen by lower alkyl, an alkyl ester of acrylic or methacrylic acid, vinylpyrrolidone or a vinyl ester.

Examples which may be mentioned are:
the acrylamide/beta-methacryloyloxyethyl-trimethylammonium methosulphate copolymer sold under the names Reten 205, 210, 220 and 240 or HERCOFLOC 812 and 815 by Hercules, the ethyl methacrylate/oleyl methacrylate/beta-methacryloyloxyethyl-diethyl-methylammonium methosulphate copolymers listed under the name Quaternium 38 in the Cosmetic Ingredient Dictionary, the ethyl methacrylate/abietyl methacrylate/beta-methacryloyloxyethyl-diethyl-methylammonium methosulphate copolymer listed under the name Quaternium 37 in the Cosmetic Ingredient Dictionary, the beta-methacryloyloxyethyl-trimethylammonium bromide polymer listed under the name Quaternium 49 in the Cosmetic Ingredient Dictionary, the beta-methacryloyloxyethyl-trimethylammonium methosulphate/beta-methacryloyloxyethyl-stearyldimethylammonium methosulphate copolymer listed under the name Quaternium 42 in the Cosmetic Ingredient Dictionary, the aminoethylacrylate phosphate/acrylate copolymer sold under the name Catrex by National Starch, which has a viscosity of 700 cps at 25° C. in 18% strength aqueous solution, and graft crosslinked cationic copolymers, having a molecular weight of 10,000 to 1,000,000 and preferably of 15,000 to 500,000, which results from the copolymerisation of:
(a) at least one cosmetic monomer,
(b) dimethylaminoethyl methacrylate,
(c) polyethylene glycol and
(d) a polyunsaturated crosslinking agent, these copolymers being described in French Pat. No. 2,189,434.

The crosslinking agent may be ethylene glycol dimethacrylate, diallyl phthalates, divinylbenzenes, tetraallyloxyethane or a polyallylsucrose having from 2 to 5 allyl groups per molecules of sucrose.

The cosmetic monomer can be of a very wide variety of types, for example a vinyl ester of an acid having from 2 to 18 carbon atoms, an allyl or methallyl ester of an acid having from 2 to 18 carbon atoms, an acrylate or methacrylate of a saturated alcohol having from 1 to 18 carbon atoms, an alkyl vinyl ether in which the alkyl radical contains from 2 to 18 carbon atoms, an olefine having from 4 to 18 carbon atoms, a vinylic heterocyclic derivative, a dialkyl or N,N-dialkylaminoalkyl maleate in which the alkyl radicals have from 1 to 3 carbon atoms, or the anhydride of an unsaturated acid.

(12°) Quaternary vinylpyrrolidone/vinylimidazole polymers such as, for example, Luviquat FC 905 sold by B.A.S.F.

(13°) Cationic silicone polymers, for example those described in European Application Nos. 17,121 and 17,122, U.S. Pat. No. 4,185,087, Japanese Patent Application No. 80/66,506 and Austrian Patent Application No. 71/01,171, and also those listed in the CTFA dictionary under the name AMODIMETHICONE, such as the product marketed as a mixture with other ingredients under the name "Dow Corning 929" cationic emulsion.

(14°) Cationic derivatives of starches or of starch ethers, such as those described in French Patent Application No. 2,434,821, in particular the polymer sold under the name LAB 358 by ROQUETTE.

(15°) Polyalkyleneimines.

(16°) Polymers containing vinylpyridine units or vinylpyridinium units in the chain.

(17°) Condensates of polyamines and epichlorohydrin.

(18°) Chitin derivatives.

(19°) Proteins and polypeptides of animal or vegetable origin, rendered cationic with a tertiary fatty amine.

The polymers of groups (9) to (15) defined above are less preferred.

The anionic polymers which can be used according to the invention are polymers containing one or more carboxylic, sulphonic or phosphoric acid groups. They generally have a molecular weight of 500 to 3,000,000.

The carboxyl groups can be introduced by means of unsaturated monocarboxylic or dicarboxylic acids represented, in particular, by the formula:

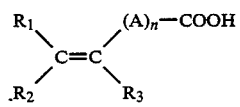

in which n is 0 or an integer from 1 to 10, A denotes a methylene group optionally joined to the carbon atom of the unsaturated group, or to the adjacent methylene group if n is greater than 1, via a heteroatom such as oxygen or sulphur, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a group —CH$_2$—COOH or a phenyl or benzyl group.

In the abovementioned formula, a lower alkyl radical preferably denotes a group having 1 to 4 carbon atoms, and in particular methyl or ethyl.

The preferred anionic polymers according to the invention are chosen, in particular, from amongst:

Homopolymers or copolymers of acrylic or methacrylic acid or their salts, and in particular the products sold under the names VERSICOL E or K by ALLIED COLLOID, ULTRAHOLD 8 by CIBA GEIGY, DARVAN No. 7 by Van der BILT, VINAPOL 1640 by SHEBY and CARBOSET 514 by GOODRICH; the acrylic acid/acrylamide copolymers sold in the form of their sodium salts under the names RETEN 421, 423 or 425 or HERCOFLOC 1018, 1031 or 1021 by HERCULES; and the acrylic or methacrylic acied/vinyl alcohol copolymers sold under the name HYDAGEN F by HENKEL.

Copolymers of the abovementioned acids with a monoethylenic monomer such as ethylene, vinylbenzene, vinyl or allyl esters or acrylic or methacrylic acid esters, optionally grafted onto a polyalkylene glycol such as polyethylene glycol, and optionally crosslinked. Such polymers are described, in particular, in French Pat. No. 1,222,944 and German Application No. 2,330,956; and copolymers of this type containing an optionally N-alkylated and/or hydroxyalkylated acrylamide unit in their chain, such as described, in particular, in Luxemburg Patent Application Nos. 75,370 and 75,371 or offered under the name QUADRAMER 5 by American Cyanamid.

Copolymers derived from crotonic acid, such as those containing, in their chain, vinyl acetate or propionate units and optionally other monomers such as allyl or methallyl esters, vinyl ether or the vinyl ester of a saturated carboxylic acid with a long hydrocarbon chain, such as those containing at least 5 carbon atoms, it being possible, if appropriate, for these polymers to be graft and crosslinked, or alternatively a vinyl, allyl or methallyl ester of an α- or β-cyclic carboxylic acid. Such polymers are described, inter alia, in French Pat. Nos. 1,222,944, 1,580,545, 2,265,782, 2,265,781, 1,564,110 and 2,439,798. Commercial products belonging to this class are the resins 28-29-30, 26-13-14 and 28-13-10 sold by National Starch.

Polymers derived from maleic, fumaric and itaconic acids or anhydrides with vinyl esters, vinyl ethers, vinyl halides, phenylvinyl derivatives, acrylic acid and its esters; these polymers can be esterified. Such polymers are described, in particular, in U.S. Pat. Nos. 2,047,398, 2,723,248 and 2,102,113 and British Pat. No. 839,805. There may be mentioned, in particular, the polymers sold under the names GANTREZ AN or ES by General Anilin or EMA 1325 by MONSANTO. Other polymers belonging to this class are copolymers of maleic, citraconic or itaconic anhydride and an allyl or methallyl ester, optionally containing an acrylamide or methacrylamide group in their chain, and monoesterified or monoamidified, these copolymers being described in French Pat. Nos. 2,350,834 and 2,357,241.

Polyacrylamides containing carboxylate groups, such as those sold by American Cyanamid under the name CYANAMER A 370.

The polymers containing a sulphonic acid group which can be used according to the invention are, in particular:

Polystyrenesulphonic acid salts such as the sodium salts sold under the name Flexan 500, which has a molecular weight of about 500,000, or under the name Flexan 130, which has a molecular weight of about 100,000, by National Starch. Such compounds are described, in particular, in French Pat. No. 2,198,729.

Alkali metal or alkaline earth metal salts of the sulphonic acids derived from lignin, and more particularly calcium or sodium lignosulphonates such as the product sold under the name Marasperse C-21 by American Can Co. and the $C_{10}$ $C_{14}$ products sold by Avébène.

Polymers containing salified alkylnaphthalenesulphonic acid units, such as the sodium salt sold under the name Darvan No. 1 by Van der Bilt.

Polymers containing at least one vinylsulphonic acid unit, such as, more particularly, polyvinylsulphonates having a molecular weight of 1,000 to 100,000, and in particular their sodium, potassium, calcium and ammonium salts and the amine salts such as the alkylamine salts and alkanolamine salts, and also copolymers containing at least some vinylsulphonic acid groups with one or more cosmetically acceptable comonomers such as unsaturated acids chosen from amongst acrylic and methacrylic acids and their esters, amides such as acrylamide or methacrylamide, which may or may not be substituted, vinyl esters, vinyl ethers and vinylpyrrolidone. These polymers are described more particularly in French Pat. No. 2,238,474 and U.S. Pat. Nos. 2,961,431 and 4,138,477.

Other anionic polymers which can be used according to the invention are chosen from amongst:

Polysaccharides of natural or synthetic, animal or vegetable origin, containing anionic groups such as carboxylate, sulphate, sulphonate or phosphate groups. In this context, there may be mentioned cellulose and carboxymethylated derivatives of cellulose (carboxymethylcelluloses) and carboxymethylhydroxyethylcelluloses, carrageenates, alginates, pectins, anionically modified starches such as carboxymethyl starches, modified guar gums such as, for example, carboxymethylated guar gums, carob gums and the xanthane gums sold, in particular, under the names KELTROLL or RHODIGEL.

It is also possible, according to the invention, to use amphoteric polymers in place of the cationic polymers or alternatively in place of the anionic polymers. In this case, it is necessary to use amphoteric polymers either with an anionic polymer if the amphoteric polymer replaces the cationic polymer, or with a cationic polymer if the amphoteric polymer replaces the anionic polymer. The amphoteric polymers consist of units A and B randomly distributed in the polymer chain, where A denotes a unit derived from a monomer containing at least one basic nitrogen atom and B denotes a unit derived from an acid monomer containing one or more carboxylic or sulphonic acid groups, or alternatively A and B can denote groups derived from zwitterionic carboxybetaine monomers; A and B can also denote a cationic polymer chain containing secondary, tertiary or quaternary amine groups, in which at least one of the amine groups carries a carboxylic or sulphonic acid group joined via a hydrocarbon radical, or alternatively A and B form part of a chain of a polymer with an $\alpha,\beta$-dicarboxyethylene unit, in which one of the carboxyl groups has been reacted with a polyamine containing one or more primary or secondary amine groups.

These polymers are described, in particular, in U.S. Pat. No. 3,836,537 and French Pat. No. 1,400,366 and also in French Patent Application No. 79/29,319. It is also possible to use amphoteric polymers of betainised dialkylaminoalkyl meth(acrylate) or dialkylaminoalkyl-meth(acrylamide), containing the following units:

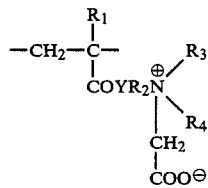

in which $R_1$ denotes a hydrogen atom or a methyl group, $R_2$ denotes an alkylene group having 1 to 4 carbon atoms, Y denotes O or NH and $R_3$ and $R_4$ independently of one another denote hydrogen or alkyl having 1 to 4 carbon atoms, and copolymers with acrylic or methacrylic acid esters containing alkyl radicals having 4 to 24 carbon atoms, and acrylic or methacrylic acid esters containing alkyl radicals having 1 to 3 carbon atoms, and optionally other monomers such as N-vinylpyrrolidone, acrylamide, hydroxyethyl or hydroxypropyl acrylate or methacrylate, acrylonitrile, styrene, chlorostyrene, vinyltoluene or vinyl acetate which copolymers are in themselves known.

The cosmetic compositions can contain pigments in addition to the cationic polymer, the anionic polymer and the waxes. The invention makes it possible to obtain a better distribution of these pigments in the composition and also to improve their attachment to the skin.

The pigments which can be used according to the invention may be inorganic pigments, organic pigments and nacreous pigments. In this context, there may be mentioned in particular, optionally surface-treated titanium dioxide (rutile or anatase) coded in the Colour Index under the reference CI 77 891, black, yellow, red and brown iron oxides coded under the references CI 77 499, 77 492 and 77 491, manganese violet (CI 77 742), ultramarine blue (CI 77 007), chromium oxide (CI 77 288), chromium hydroxide (CI 77 289) and Prussian blue (CI 77 510). The organic pigments are chosen, in particular, from amongst the pigments D and C Red No. 19 (CI 45 170), D and C Red No. 9 (CI 15 585), D and C Red No. 21 (CI 45 380), D and C Orange No. 4 (CI 15 510), D and C Orange No. 5 (CI 45 370), D and C Red No. 27 (CI 45 410), D and C Red No. 13 (CI 15 630), D and C Red No. 7 (CI 15 850), D and C Red No. 6 (CI 15 850), D and C Yellow No. 5 (CI 19 140), D and C Red No. 36 (CI 120 85), D and C Orange No. 10 (CI 45 425), D and C Yellow No. 6 (CI 15 985), D and C Red No. 30 (CI 73 360) and D and C Red No. 3 (CI 45 430) and lakes based on carmine (CI 75 470).

The nacreous pigments can be chosen from amongst white nacreous pigments such as mica covered with titanium oxide, and bismuth oxychloride, coloured nacreous pigments such as titanium mica with iron oxides, titanium mica with Prussian blue or chromium oxide, and titanium mica with an organic pigment of the abovementioned type, and also those based on bismuth oxychloride.

If used, the pigments are suitably present in proportions of 3 to 20% relative to the total weight of the composition, depending on the colouration and the intensity of the colouration which it is desired to obtain.

The compositions according to the invention can be produced in a variety of forms suitable, in particular, for making up the skin, eyelashes and eyebrows.

These compositions can be presented, in particular, in the form of an anhydrous solid or paste or in the form of oil-in-water or water-in-oil emulsions. If they are used in the form of emulsions, they can contain surface-active agents which are well known in the state of the art, and which may be anionic, non-ionic or amphoteric surface-active agents or mixtures thereof. These compositions preferably do not contain a cationic surface-active agent.

A particularly preferred embodiment consists in preparing anionic or non-ionic emulsions using antionic or non-ionic surface-active agents, preferably in proportions of 2 to 30% by weight.

Amongst the anionic surface-active agents which can be used singly or in a mixture, there may be mentioned in particular, the alkali metal salts, the ammonium salts, the amine salts or the aminoalcohol salts of the following compounds:

alkyl-sulphates, alkyl-ether-sulphates, alkylamidesulphates and alkylamido-ether-sulphates, alkylaryl-polyether-sulphates and monoglyceride-sulphates, alkylsulphonates, alkylamidesulphonates, alkylarylsulphonates, $\alpha$-olefinesulphonates and paraffinsulphonates, alkyl-sulphosuccinates, alkyl-ether-sulphosuccinates and alkylamide-sulphosuccinates, alkyl-sulphosuccinamates, alkyl-sulphoacetates and alkyl-polyglycerol-carboxylates, alkyl-phosphates/alkyl-ether-phosphates, and alkylsarcosinates, alkylpolypeptidates, alkylamidopolypestidates, alkylisethionates and alkyltaurates.

The alkyl radical in all these compounds generally has 12 to 18 carbon atoms.

Other anionic surface-active agents include salts of fatty acids such as oleic acid, ricinoleic acid, palmitic acid, stearic acid and the acids from copra oil or from hydrogenated copra oil, and in particular amine salts such as amine stearates.

The following may also be mentioned:
acyllactylates in which the acyl radical contains from 8 to 20 carbon atoms, and
carboxylic acids of polyglycol ethers, corresponding to the formula:

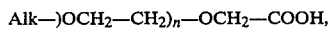
Alk—)OCH$_2$—CH$_2$)$_n$—OCH$_2$—COOH, in the form of bases or salts, in which the substituent Alk corresponds to a linear alkyl chain having from 12 to 18 carbon atoms and in which n is an integer from 5 to 15.

Amongst the non-ionic surface-active agents which can be used by themselves or in a mixture, there may be mentioned, in particular: polyoxyethyleneated, polyoxypropyleneated or polyglycerolated alcohols, alkylphenols and fatty acids having a fatty chain containing 8 to 18 carbon atoms. There may also be mentioned ethylene oxide/propylene oxide copolymers, condensates of ethylene oxide and propylene oxide with fatty alcohols, polyoxyethyleneated fatty amides, polyoxyethyleneated fatty amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters and fatty acid esters of glucose derivatives.

Other compounds belonging to this class are: the condensation products of a monoalcohol, an α-diol, an alkylphenol, an amide or a diglycolamide with glycidol, such as:

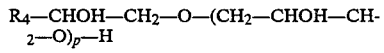
R$_4$—CHOH—CH$_2$—O—(CH$_2$—CHOH—CH$_2$—O)$_p$—H in which R$_4$ denotes an aliphatic, cycloaliphatic or arylaliphatic radical preferably having 7 to 21 carbon atoms, and mixtures thereof, it being possible for the aliphatic chains to contain ether, thioether or hydroxymethylene groups, and in which p is from 1 to 10 inclusive, such as described in French Pat. No. 2,091,516 or U.S. Pat. No. 3,821,372;
products corresponding to the formula:

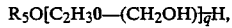
R$_5$O[C$_2$H$_3$0—(CH$_2$OH)]$_q$H, in which R$_5$ denotes an alkyl, alkenyl or alkylaryl radical and q has a statistical value of 1 to 10 inclusive such as described in French Pat. No. 1,477,048; or U.S. Pat. No. 3,578,719 and
products corresponding to the formula:

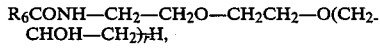
R$_6$CONH—CH$_2$—CH$_2$O—CH$_2$CH$_2$—O(CH$_2$-CHOH—CH$_2$)$_r$H, in which R$_6$ denotes a linear or branched, saturated or unsaturated aliphatic radical, or a mixture of such radicals, which can optionally contain one or more hydroxyl groups, has 8 to 30 carbon atoms and is of natural or synthetic origin, and r represents an integer, or decimal number (denoting the average degree of condensation), from 1 to 5 such as described in French Pat. No. 2,328,763 or U.S. Pat. No. 4,307,079.

The non-ionic emulsions consist mainly of a mixture of oils and/or fatty alcohols, or alternatively or polyoxyethyleneated or polyglycerolated alcohols such as polyoxyethyleneated stearyl or cetyl-stearyl alcohols.

The anionic emulsions are preferably made up from amine stearates.

In addition to the abovementioned components, the compositions can contain ingredients conventionally used especially in make-up compositions, including oils, silicones, thickeners, softeners, anti-sunburn products, perfumes, preservatives, sequestering agents, non-ionic polymers and also alkalising or acidifying agents normally used in the cosmetics field, depending on the application envisaged.

The thickeners which can be used include sodium alginate, gum arabic or cellulose derivatives such as methylcellulose, hydroxymethylcellulose, hydroxyethylcellulose, hydroxypropylcellulose or hydroxypropylmethylcellulose. The compositions can also be thickened using a mixture of polyethylene glycol and polyethylene glycol stearate or distearate or a mixture of phosphoric acid esters and fatty amides.

The oils are suitably vegetable or mineral oils and especially hydrogenated palm oil, hydrogenated castor oil, vaseline oil and paraffin oil.

The particularly preferred compositions are those comprising, as the cationic polymer, the polymers derived from cellulose ether, containing quaternary ammonium groups, and the optionally crosslinked polyaminopolyamides defined above.

The preferred anionic polymers are chosen, in particular, from acrylic or methacrylic acid polymers or copolymers such as those sold under the name Versicol, Vinapol 1640 or Darvan No. 7, carboxymethylcelluloses, modified guar gums, in particular carboxymethylated guar gums, and xanthane gums such as those sold under the name Keltroll.

According to a preferred embodiment of the invention, animal, vegetable, microcrystalline or synthetic waxes are used with the preferred cationic and anionic polymers mentioned above.

The compositions according to the invention are particularly suitable for use as mascara presented in the form of an anhydrous solid or paste or of oil-in-water or water-in-oil emulsions.

In addition to the waxes, the cationic polymer and the anionic polymer, such compositions contain thickeners and pigments making it possible to obtain the desired colouration.

These mascaras make it possible, in particular, to lengthen the eyelashes. The particularly preferred mascaras are compositions containing polymeers derived from cellulose ether and containing quaternary ammonium groups, in association with a sodium polymethacrylate such as that sold under the name DARVAN No. 7.

Another application of the invention is the use of the compositions as eye shadows. These compositions are preferably presented in the form of water-in-oil or oil-in-water emulsions and contain waxes, a cationic polymer and an anionic polymer, pigments and an anionic or non-ionic suface-active agent.

Finally, the compositions can be used as lipsticks, as rouges, as face creams and especially as products which firm the skin and reduce the small wrinkles with a stretching effect.

In addition to the waxes, the anionic polymer and the cationic polymer, such compositions contain oils and surface-active agents.

The Examples which follow further illustrate the present invention.

EXAMPLE 1

The following composition is prepared:

| | |
|---|---|
| Triethanolamine stearate | 30.00 g |
| Microcrystalline wax (melting point 89° C.) | 20.00 g |
| Beeswax (melting point 61–65° C.) | 5.00 g |
| Carnauba wax (melting point 83–86° C.) | 10.00 g |
| Methyl para-hydroxybenzoate | 0.15 g |
| Propyl para-hydroxybenzoate | 0.15 g |
| Gum arabic | 4.70 g |
| Darvan 7 | 1.00 g |
| Polymer JR 400 | 1.00 g |
| Red iron oxide | 5.00 g |
| Black iron oxide | 5.00 g |
| | 82.00 g |

To prepare the composition, the various constituents are melted at 90° C. and mixed.

This composition is in the form of a cake used as mascara.

The eyelashes made up using this composition are considerably lengthened.

EXAMPLE 2

The following composition is prepared:

| | |
|---|---|
| Carnauba wax (melting point 83–86° C.) | 15.00 g |
| Candelilla wax (melting point 66–71° C.) | 7.00 g |
| Triethanolamine stearate | 10.00 g |
| Darvan 7 | 1.00 g |
| Polymer JR 400 | 1.00 g |
| Hydroxyethylcellulose | 0.20 g |
| Aminosilicate polysulphide | 4.00 g |
| Black iron oxide | 5.00 g |
| Imidazolidinylurea | 0.30 g |
| Softened water qsp | 100 g |

This composition, used as automatic mascara, is obtained by heating the fatty substances with the pigments to 90° C. and by adding the emulsifiers and the other water-soluble components with vigorous stirring. When it is applied to the eyelashes, it is observed that they are lengthened.

EXAMPLE 3

The following composition is prepared:

| | |
|---|---|
| Fatty acid ester of sorbitan | 4.00 g |
| Microcrystalline wax (melting point 89° C.) | 5.00 g |
| Beeswax (melting point 61–65° C.) | 2.00 g |
| Paraffin oil | 8.00 g |
| Methyl para-hydroxybenzoate | 0.30 g |
| Titanium mica | 10.00 g |
| Polyethylene powder | 5.00 g |
| Vinapol 1640 | 0.50 g |
| Polymer A* | 0.50 g |
| Softened water qsp | 100 g |

A water-in-oil emulsion is prepared with the above-mentioned constituents by heating the fatty substances and the emulsifier to about 90° C. and by adding the water and the other components with vigorous stirring.

This product is used as an eye shadow.

EXAMPLE 4

The following composition is prepared:

| | |
|---|---|
| Isopropyl palmitate | 22.00 g |
| Paraffin oil | 26.00 g |
| Sweet-almond oil | 0.50 g |
| Ozokerite (melting point 73–74° C.) | 2.00 g |
| Lanoline alcohol | 6.50 g |
| Silicone oil | 2.00 g |
| Magnesium lanolate | 2.90 g |
| Sodium polyvinylsulphonate | 0.5 g |
| Cationic polymer JR 400 | 0.8 g |
| Preservatives | qs |
| Perfume | qs |
| Sterile demineralised water qsp | 100 g |

This composition, which is in the form of an emulsion, is used as a cream for firming the face.

EXAMPLE 5

The following composition is prepared by heating the fatty substances with the pigments to 90° C. and then adding the emulsifiers and the other water-soluble components with vigorous stirring:

| | |
|---|---|
| Stearic acid | 3 g |
| Microcrystalline wax (melting point 89° C.) | 1 g |
| Hydrogenated palm oil | 2 g |
| Triethanolamine | 1.2 g |
| Polyethylene glycol 1500 | 15 g |
| Magnesium silicate | 0.6 g |
| Methyl para-hydroxybenzoate | 0.1 g |
| Propyl para-hydroxybenzoate | 0.1 g |
| Imidazolidinylurea | 0.3 g |
| Aluminosilicate polysulphide | 2 g |
| Titanium dioxide | 3 g |
| Titanium mica | 15 g |
| Darvan 7 | 0.5 g |
| LAB 358 | 0.5 g |
| Sterile softened water qsp | 100 g |

This composition is in the form of an emulsion and is used as an eye shadow.

EXAMPLE 6

The following composition is prepared by heating the fatty substances with the pigments to 90° C. and then adding the emulsifiers and the other water-soluble components with vigorous stirring:

| | |
|---|---|
| Candelilla wax (melting point 66/71° C.) | 5 g |
| Microcrystalline wax (melting point 89° C.) | 10 g |
| Beeswax (melting point 61/65° C.) | 10 g |
| A.M.P. stearate | 10 g |
| Hydroxypropylcellulose | 0.8 g |
| Methyl para-hydroxybenzoate | 0.1 g |
| Propyl para-hydroxybenzoate | 0.1 g |
| Black iron oxide | 5 g |
| Darvan 7 | 0.2 g |
| Hercofloc 812 | 0.2 g |
| Sterile softened water qsp | 100 g |

This composition is in the form of an oil-in-water emulsion. It is used as automatic mascara.

EXAMPLE 7

The following composition is prepared by heating the fatty substances with the pigments to 90° C. and then adding the emulsifiers and the other water-soluble components with vigorous stirring:

| | |
|---|---|
| Candelilla wax (melting point 66/71° C.) | 14 g |
| Ozokerite (melting point 73/74° C.) | 3 g |
| Resin P 8011 | 1 g |
| Resin P 27 24 | 1 g |
| Talc | 3 g |
| Organically modified bentonite | 2 g |
| Propylene carbonate | 0.5 g |
| Black iron oxide | 5 g |
| Aluminosilicate polysulphide | 2 g |
| Butylhydroxytoluene | 0.030 g |
| Gantrez ES 425 | 0.5 g |
| Dow Corning 929 | 0.5 g |
| Isoparaffin qsp | 100 g |

To prepare this composition, the bentonite is dispersed in a mixture of isoparaffin and propylene carbonate; this gives a gel to which the other constituents are added, with moderate heating and with stirring.

This composition is used as a waterproof mascara.

EXAMPLE 8

The following composition is prepared by mixing the various constituents by heating to 50°–60° C.:

| | |
|---|---|
| Glycerol trilaurate | 15 g |
| Hydrogenated tallow | 5 g |
| Lanoline wax | 6 g |
| Carnauba wax (melting point 83/86° C.) | 15 g |
| Talc | 10 g |
| Butylhydroxytoluene | 0.05 g |
| Aluminosilicate polysulphide | 3 g |
| Titanium dioxide | 5 g |
| Titanium mica | 15 g |
| Gantrez ES 425 | 0.5 g |
| Gafquat 755 | 0.5 g |
| Isoparaffin qsp | 100 g |

This composition is used as a waterproof eye shadow.

EXAMPLE 9

The following composition is prepared by heating the fatty substances with the pigments to 90° C. and then adding the emulsifiers and the other water-soluble components with vigorous stirring:

| | |
|---|---|
| Stearic acid | 1 g |
| Carnauba wax (melting point 83/86° C.) | 1 g |
| Hydrogenated castor oil | 3 g |
| Triethanolamine | 0.4 g |
| Methylhydroxypropylcellulose | 2.5 g |
| Polyethylene glycol 1500 | 12 g |
| Methyl para-hydroxybenzoate | 0.1 g |
| Propyl para-hydroxybenzoate | 0.1 g |
| Ethyl para-hydroxybenzoate | 0.1 g |
| Magnesium silicate | 0.5 g |
| Titanium dioxide | 10 g |
| Aluminosilicate polysulphide | 2 g |
| Black iron oxide | 2 g |
| Hercofloc 1018 | 0.1 g |
| Merquat 550 | 0.5 g |
| Sterile softened water qsp | 100 g |

This composition, which is in the form of an oil-in-water emulsion, is used as eye liner.

EXAMPLE 10

The following composition is prepared by heating the fatty substances with the pigments to 90° C. and then adding the emulsifiers and the other water-soluble components with vigorous stirring:

| | |
|---|---|
| Microcrystalline wax (melting point 89° C.) | 1 g |
| Paraffin (melting point 60° C.) | 5 g |
| Glycerol isostearate (self-emulsifiable) | 4 g |
| Vaseline oil (liquid petrolatum) | 20 g |
| Isopropyl myristate | 5 g |
| Imidazolidinylurea | 0.3 g |
| Methyl para-hydroxybenzoate | 0.15 g |
| Brown iron oxide | 1 g |
| DC Red 7 | 0.2 g |
| Titanium dioxide | 3 g |
| Titanium mica | 10 g |
| Darvan 2 | 0.5 g |
| Luviquat FC 905 | 0.5 g |
| Sterile softened water qsp | 100 g |

This composition, which is in the form of an oil-in-water emulsion, is used as rouge.

EXAMPLE 11

The following composition is prepared by heating the fatty substances with the pigments to 90° C. and then adding the emulsifiers and the other water-soluble components with vigorous stirring:

| | |
|---|---|
| Paraffin oil | 17 g |
| Microcrystalline wax (melting point 89° C.) | 3 g |
| Saturated fatty acid glycerides | 5 g |
| Magnesium lanolate | 4 g |
| Hydrogenated lanoline | 3 g |
| Methyl para-hydroxybenzoate | 0.3 g |
| Iron oxide | 2.5 g |
| Titanium dioxide | 5 g |
| Carboset 525 | 0.5 g |
| Polyethyleneimine | 0.5 g |
| Sterile softened water qsp | 100 g |

This composition, which is in the form of a water-in-oil emulsion, is used as rouge.

EXAMPLE 12

The following composition is prepared by heating the fatty substances with the pigments to 90° C. and then adding the emulsifiers and the other water-soluble components with vigorous stirring:

| | |
|---|---|
| Stearic acid | 10 g |
| Candelilla wax (melting point 66/71° C.) | 3 g |
| Beeswax (melting point 61/65° C.) | 5 g |
| Microcrystalline wax (melting point 89° C.) | 10 g |
| Triethanolamine | 3 g |
| Guar gum | 3 g |
| Methylcellulose | 0.2 g |
| Methyl para-hydroxybenzoate | 0.1 g |
| Propyl para-hydroxybenzoate | 0.1 g |
| Black iron oxide | 6 g |
| Flexan 130 | 0.5 g |
| Polymer called AZA | 0.5 g |
| Sterile softened water qsp | 100 g |

This composition, which is in the form of an oil-in-water emulsion, is used as an automatic mascara.

EXAMPLE 13

The following composition is prepared by heating the fatty substances with the pigments to 90° C. and then adding the emulsifiers and the other water-soluble components with vigorous stirring:

| | |
|---|---|
| Fatty acid ester of glycerol | 6 g |
| Polyoxyethyleneated fatty acid ester | 3 g |
| Montan wax (melting point 85° C.) | 3 g |
| Candelilla wax (melting point 66/71° C.) | 3 g |
| Microcrystalline wax (melting point 89° C.) | 12 g |
| Carob gum | 5 g |
| Methyl para-hydroxybenzoate | 0.1 g |
| Propyl para-hydroxybenzoate | 0.1 g |
| Ethyl para-hydroxybenzoate | 0.1 g |
| Black iron oxide | 4 g |
| Aluminosilicate polysulphide | 3 g |
| Jaguar C 13S | 0.5 g |
| Darvan 1 | 0.5 g |
| Sterile softened water qsp | 100 g |

This composition, which is in the form of an oil-in-water emulsion, is used as automatic mascara.

EXAMPLE 14

The following composition is prepared by heating the fatty substances with the pigments to 90° C. and then adding the emulsifiers and the other water-soluble components with vigorous stirring:

| | |
|---|---|
| Carnauba wax (melting point 83/85° C.) | 10 g |
| Ceresine (melting point 70/73° C.) | 9 g |
| Triethanolamine stearate | 12 g |
| Hydroxyethylcellulose | 2 g |
| Black iron oxide | 10 g |
| Methyl para-hydroxybenzoate | 0.3 g |
| Sodium mercurothiolate | 0.002 g |
| Amersette TM | 0.5 g |
| Darvan 7 | 0.5 g |
| Sterile softened water qsp | 100 g |

This composition is used as automatic mascara.

EXAMPLE 15

The following composition is prepared by heating the fatty substances with the pigments to 90° C. and then adding the emulsifiers and the other water-soluble components with vigorous stirring:

| | |
|---|---|
| Carnauba wax (melting point 83/86° C.) | 10 g |
| Ceresine (melting point 70/73° C.) | 9 g |
| Triethanolamine stearate | 12 g |
| Hydroxyethylcellulose | 2 g |
| Black iron oxide | 10 g |
| Methyl para-hydroxybenzoate | 0.3 g |
| Sodium mercurothiolate | 0.002 g |
| Amersette TM | 0.5 g |
| JR 400 | 0.5 g |
| Sterile softened water qsp | 100 g |

This composition is used as automatic mascara.

EXAMPLE 16

The following composition is prepared by heating the fatty substances with the pigments to 90° C. and then adding the emulsifiers and the other water-soluble components with vigorous stirring:

| | |
|---|---|
| Vaseline oil | 20 g |
| Alkyl myristate | 6 g |
| Beeswax (melting point 61/65° C.) | 10 g |
| Sodium borate | 1 g |
| Propyl para-hydroxybenzoate | 0.15 g |
| Imidazolidinylurea | 0.30 g |
| Iron oxides | 5 g |
| Titanium dioxide | 5 g |
| Darvan 7 | 0.2 g |

-continued

| | |
|---|---|
| Lexein CP 125 | 1 g |
| Sterile softened water qsp | 100 g |

This composition is used as a shadow concealer for the eyes.

EXAMPLE 17

The following composition is prepared by melting the various constituents at 50°–60° C. and stirring to homogenise them:

| | |
|---|---|
| Carnauba wax (melting point 83/86° C.) | 17 g |
| Ozokerite (melting point 73/74° C.) | 16 g |
| Lanoline | 24 g |
| Paraffin oil | 24 g |
| Gantrez ES 425 (GAF) | 0.5 g |
| Dow Corning 929 | 0.5 g |
| Isoparaffin | 5 g |
| Permitted pigments | 8 g |
| Titanium dioxide | 4 g |
| Perfume | 1 g |

This composition is used in the form of a lipstick.

EXAMPLE 18

The following composition is prepared by heating the fatty substances with the pigments to 90° C. and then adding the emulsifiers and the other water-soluble components with vigorous stirring:

| | |
|---|---|
| Fatty acid ester of sorbitan | 4 g |
| Alkyl myristate | 10 g |
| Isopropyl myristate | 10 g |
| Ozokerite (melting point 73/74° C.) | 4 g |
| Carnauba wax (melting point 83/86° C.) | 1 g |
| Imidazolidinylurea | 0.3 g |
| Methyl para-hydroxybenzoate | 0.1 g |
| Titanium dioxide | 3 g |
| Titanium mica | 10 g |
| Resyn 28.29.30 | 0.5 g |
| Cartaretine F4 | 0.5 g |
| Sterile softened water qsp | 100 g |

This composition, which is in the form of a water-in-oil emulsion, is used as an eye shadow.

EXAMPLE 19

The following composition is prepared by heating the fatty substances with the pigments to 90° C. and then adding the emulsifiers and the other water-soluble components with vigorous stirring:

| | |
|---|---|
| Fatty acid ester of sorbitan | 4 g |
| Microcrystalline wax (melting point 89° C.) | 5 g |
| Ozokerite (melting point 73/74° C.) | 2 g |
| Alkyl myristate | 5 g |
| Paraffin oil | 20 g |
| Imidazolidinylurea | 0.3 g |
| Methyl para-hydroxybenzoate | 0.1 g |
| Black iron oxide | 0.2 g |
| Brown iron oxide | 0.5 g |
| Yellow iron oxide | 1 g |
| Titanium dioxide | 3 g |
| Titanium mica | 5 g |
| Polyethylene powder | 5 g |
| Cyanamer A 370 | 0.5 g |
| Delsette 101 | 1 g |
| Sterile softened water qsp | 100 g |

This composition, which is in the form of a water-in-oil emulsion, is used as a shadow concealer for the eyes.

The names which are used in the preceding examples denote the following products:

| | |
|---|---|
| *Polymer A: | Polycondensate of equimolar amounts of adipic acid and diethylenetriamine, crosslinked with epichlorohydrin at a rate of 11 mols of epichlorohydrin per 100 amine groups chlorohydrin per 100 amine groups of the polyaminopolyamide. |
| DARVAN 7: | A sodium polymethacrylate sold by VANDERBILT. |
| LAB 358: | A cationic starch ether sold by ROQUETTE. |
| HERCOFLOC 812, also called QUATERNIUM 39: | According to the CTFA dictionary, an acrylamide/methacrylyloxyethyl-trimethyl-ammonium methosulphate copolymer. |
| RESINE P 8011: | A polyvinyl laurate. |
| RESINE P 27 24: | A vinyl acetate/allyl stearate copolymer. |
| GANTREZ ES 425: | The monobutyl ester of poly-(methyl vinyl ether/maleic acid), sold by GAF. |
| DOW CORNING 929: | A cationic silicone polymer |
| GAFQUAT 755: | A quaternary polyvinylpyrrolidone copolymer having a molecular weight of about 1,000,000, sold by GAF. |
| HERCOFLOC 1018: | An acrylic acid/acrylamide copolymer sold by HERCULES. |
| MERQUAT 550: | A dimethyldiallylammonium chloride/ acrylamide copolymer having a molecular weight of more than 500,000, sold by MERCK. |
| DARVAN 2: | An alkali metal salt or alkaline earth metal salt of a sulphonic acid derived from lignin, sold by VANDERBILT. |
| LUVIQUAT FC 905: | A quaternised vinylpyrrolidone/ Vinylimidazole copolymer sold by BASF. |
| CARBOSET 525: | An acrylic acid/acrylate copolymer sold by GOODRICH. |
| FLEXAN 130: | A sodium salt of polystyrenesulphonate having a molecular weight of the order of 100,000, sold by National Starch. |
| Polymer AZA: | A cationic polycondensate of piperazine/diglycolamine/epichlorohydrin in the molar proportions of 4/1/5, described in Example 2 of French Patent No. 2,280,361. |
| JAGUAR C 13S: | Quaternised quar gum derivative sold by CELANESE. |
| DARVAN 1: | A polymer containing alkylenenaphthalenesulphonic acid units, sold by VANDERBILT. |
| AMERSETTE TM: | An amphoteric methacrylate resin with a betaine-type structure, sold by AMERCHOL. |
| LEXEIN CP 125: | A mixture of proteins and polypeptrides of animal and vegetable origin, quaternised with a tertiary fatty amine, sold by INOLEX. |
| RESYN 28.29.30: | A vinyl acetate/crotonic acid/vinyl neodecanoate terpolymer sold by NATIONAL STARCH. |
| CARTARETINE F4: | An adipic acid/dimethylaminohydroxypropyldiethylenetriamine copolymer sold by SANDOZ. |
| CYANAMER A 370: | A modified polyacrylamide having a molecular weight of about 200,000 and a specific viscosity of 3.7 ± 0.5, sold by AMERICAN CYANAMID. |
| DELSETTE 101: | An adipic acid/epoxypropyldiethylenetriamine copolymer sold by HERCULES. |

The disclosure in the Patent Specifications referred to herein is all incorporated by reference.

The "needle penetration" according to ASTM Method D 5 such as used in the present application is the depth in tenth of a millimeter, to which a standard needle (Weighing together with its equiment 50 g) placed during 5 secondes on the surface of the wax penetrates into the wax.

We claim:

1. In a wax based cosmetic composition containing a polymer and from about 5 to 40% by weight of a wax selected from the group consisting of vegetable, animal, mineral and synthetic wax, said wax having a melting point of 60 to 110 degrees C., and a needle penetration according to ASTM Method D5 at 25 degrees C. of 3 to 40 and said wax being solid and rigid at a temperature below 50 degrees C., wherein the improvement comprises said polymer being the combination of a cationic polymer and an anionic polymer, said cationic polymer being present in the cosmetic composition in an amount of about 0.1 to 10% by weight and having a molecular weight of 1,000 to 3,000,000, said cationic polymer being a polymer of the polyamine, polyamino-polyamide or poly-(quaternary ammonium) type, the amine or ammonium group forming a part of or being joined to the polymer chain, said anionic polymer being present in the cosmetic composition in an amount of about 0.1 to 10% by weight and having a molecular weight of 500 to 3,000,000, said anionic polymer containing carboxylic, sulphonic or phosphoric acid groups.

2. A composition according to claim 1, in which the cationic polymer is:
   (1) a quaternised or unquaternised vinylpyrrolidone/-dialkylaminoalkyl acrylate or methacrylate copolymer;
   (2) a cellulose ether derivative containing quaternary ammonium groups, or a quaternary cellulose derivative;
   (3) a cationic polysaccharide;
   (4) a cationic polymer containing units of the formula —A—Z—A—Z—(I), in which A denotes a radical containing two amino groups, and Z denotes the symbol B or B', B and B', which are identical or different, denoting a linear or branched alkylene radical which is unsubstituted or substituted by an hydroxyl group and which can also contain a member selected from the group consisting of oxygen, nitrogen and sulphur atoms and 1 to 3 aromatic or heterocyclic rings; or a polymer of the formula —A—$Z_1$—A—$Z_1$—(II), in which A is as defined above and $Z_1$ denotes the symbol $B_1$ or $B'_1$ and denotes $B'_1$ at least once, $B_1$ being a linear or branched alkylene or hydroxyalkylene radical; $B'_1$ denotes a linear or branched alkylene radical which is unsubstituted or substituted by an hydroxyl radical and which is interrupted by a nitrogen atom, the nitrogen atom being substituted by an alkyl radical, the alkyl radical interrupted by an oxygen atom and containing a hydroxyl group; or a quaternary ammonium salt or oxidation product of a polymer of formula (I) or (II);
   (5) a polyaminopolyamide;
   (6) a crosslinked polyaminopolyamide which is:
      (a) an alkylated, crosslinked polyaminopolyamide obtained by crosslinking a polyaminopolyamide prepared by the polycondensation of an acid with a polyamine, with a crosslinking agent which is an epihalogenohydrin, diepoxide, dianhydride, unsaturated anhydride or bis-unsaturated derivative, the crosslinking agent being used in an amount from 0.025 to 0.35 mol per amine group of the polyaminopolyamide;
(b) a water-soluble crosslinked polyaminopolyamide obtained by crosslinking a polyaminopolyamide defined above with a crosslinking agent which is:
I—a bis-halogenohydrin, bis-azetidinium compound, bis-halogenoacyldiamine or bis-(alkyl halide),
II—an oligomer obtained by reacting a compound from group I or an epihalogenohydrin, diepoxide or bis-unsaturated derivative with a difunctional compound reactive towards said compound, and
III—a quaternisation product of a compound from group I and an oligomer from group II, containing tertiary amine groups which can be totally or partially alkylated, with an alkylating agent, the crosslinking being carried out using 0.025 to 0.35 mol of crosslinking agent per amine group of the polyaminopolyamide; or
(c) a polyaminopolyamide derivative resulting from the condensation of a polyalkylene-polyamine with a polycarboxylic acid, followed by alkylation with a difunctional agent;
(7) a polymer obtained by reacting a polyalkylenepolyamine containing two primary amine groups and at least one secondary amine group with a dicarboxylic acid which is diglycolic acid or a saturated aliphatic dicarboxylic acid having 3 to 8 carbon atoms, the molar ration of the polyalkylenepolyamine to the dicarboxylic acid being from 0.8:1 to 1.4:1, the resulting polyaminopolyamide being reacted with epichlorohydrin in a molar ratio of epichlorohydrin to the secondary amine groups of the polyaminopolyamide of 00.5:1 to 1.8:1;
(8) a cyclic polymer containing units corresponding to the formula (III) or (III')

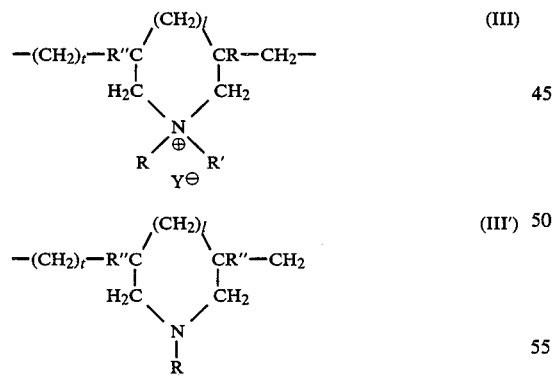

in which and t are equal to 0 or 1 with +t+1, R" denotes hydrogen or methyl, R and R' independently of one another denote an alkyl group having 1 to 22 carbon atoms, a hydroxyalkyl group, or a lower amidoalkyl group, or R or R' denote, together with the nitrogen atom to which they are attached, a heterocyclic group, or a copolymer containing units of the formula (III) or (III') and units derived from acrylamide or from diacetone-acrylamide, and Y⁻ is an anion;
(9) a poly-(quaternary ammonium) compound of the formula:

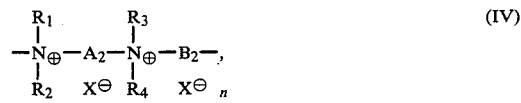

in which $R_1$ and $R_2$, and $R_3$ and $R_4$, which are identical or different, represent aliphatic, alicyclic or arylaliphatic radicals containing up to 20 carbon atoms, or lower hydroxyaliphatic radicals, or alternatively $R_1$ and $R_2$, and $R_3$ and $R_4$, together or separately form, with the nitrogen atoms to which they are attached, a heterocyclic ring containing a second heteroatom other than nitrogen, or alternatively, $R_1$, $R_2$, $R_3$ and $R_4$, represent a group:

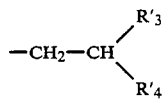

$R'_3$ denotingg hydrogen or lower alkyl and $R'_4$ denoting:

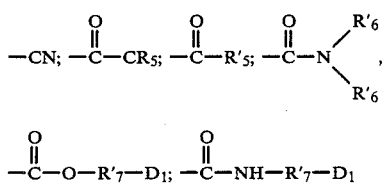

$$-C-O-R'_7-D_1; -C-NH-R'_7-D_1$$

$R'_5$ denoting lower alkyl, $R'_6$ denoting hydrogen or lower alkyl, $R'_7$ denoting alkylene and $D_1$ denoting a quaternary ammonium group, $A_2$ and $B_2$ independently represent an aliphatic group containing from 2 to 20 carbon atoms, which can be linear or branched and saturated or unsaturated and which contain, inserted in the main chain an aromatic ring, or a group:

$$-(CH_2)_n-Y_1-(CH_2)_n-,$$

with $Y_1$ denoting O, S, SO, $SO_2$

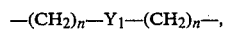

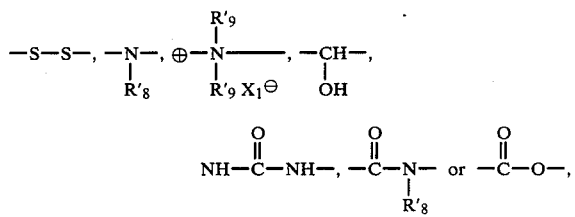

with $X_1$ denoting an anion derived from a mineral or organic acid, n being 2 or 3, $R'_8$ denoting hydrogen or lower alkyl and $R'_9$ denoting lower alkyl, or alternatively $A_2$ and
$R_1$ and $R_3$ form a piperazine ring with the two nitrogen atoms to which they are attached; and, if $A_2$ denotes a linear or branched, saturated or unsaturated aliphatic or hydroxyaliphatic radical, $B_2$ can also denote a group:

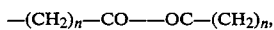

in which $D_2$ denotes:

(a) a glycol radical of the formula —O—Z—O—, in which Z denotes a linear or branched hydrocarbon radical or a group corresponding to the formula:

$$-(CH_2-CH_2-O)_x CH_2-CH_2-\text{ or}$$

$$-(CH_2-\underset{\underset{CH_3}{|}}{CH}-O)_y CH_2-\underset{\underset{CH_3}{|}}{CH}-,$$

in which x and y denote an integer from 1 to 4;
(b) a bis-secondary diamino radical;
(c) a bis-primary diamine radical of the formula:

—NH—Y—NH—, in which Y denotes a linear or branched hydrocarbon radical or the divalent radical —CH$_2$—CH$_2$—S—S—CH$_2$—CH$_2$—; or
(d) a ureylene group of the formula —NH—CO—NH—; n is such that the molecular weight is from 1,000 to 100,000 and X$^-$ denotes an anion;

(10) a homopolymer or copolymer derived from acrylic or methacrylic acid and containing a unit:

$$-CH_2-\underset{\underset{\underset{\underset{\underset{R_5 \quad R_6}{\diagup \diagdown}}{N}}{A_1}}{C=O}}{\overset{R_7}{|}}-,\quad -CH_2-\underset{\underset{\underset{\underset{R_9}{|}}{R_8-N^{\oplus}-R_{10}}}{A_1}}{\overset{R_7}{|}}-\text{ or } -CH_2-\underset{\underset{\underset{\underset{R_9}{|}}{R_8-N^{\oplus}-R_{10}}}{\underset{NH}{|}}}{\overset{R_7}{|}} X_1^{\ominus} \quad (V)$$

in which R$_7$ is H or CH$_3$, A$_1$ is a linear or branched alkyl group having 1 to 6 carbon atoms or a hydroxyalkyl group having 1 to 4 carbon atoms, R$_8$, R$_9$ and R$_{10}$, which are identical or different, denote an alkyl group having 1 to 18 carbon atoms or a benzyl group, R$_5$ and R$_6$ denote H or alkyl having 1 to 6 carbon atoms, and X$_1^-$ denotes a methosulphate or halide anion;
(11) a quaternary vinylpyrrolidione/vinylimidazole copolymer;
(12) a polyalkyleneimine;
(17) a protein or polypeptide of animal or vegetable origin, rendered cationic with a tertiary fatty amine;
(18) a cationic silicone polymer; or
(19) a cationic derivative of starch or starch ether.

3. A composition according to claim 1, which further comprises a mineral, organic or nacreous pigment in an amount from 3 to 20% by weight, relative to the total weight of the composition.

4. A composition according to claim 1, in which the polymer containing a carboxylic acid group is derived from an unsaturated monocarboxylic or dicarboxylic acid represented by the formula:

$$\underset{R_2}{\overset{R_1}{\diagdown}} C=C \underset{R_3}{\overset{(A)_n-COOH}{\diagup}}$$

in which n is 0 or an integer from 1 to 10, A denotes a methylene group joined directly to the carbon atom of the unsaturated group or to the adjacent methylene group if n is greater than 1, via a heteroatom, R$_1$ denotes a hydrogen atom or a phenyl or benzyl group, R$_2$ denotes a hydrogen atom or a lowr alkyl or carboxyl group and R$_3$ denotes a hydrogen atom, a lower alkyl group, a group OCH$_2$-COOH or a phenyl or benzyl group;

the polymer containing a sulphonic acid group is:
  a polystyrenesulphonic acid salt,
    an alkali metal or alkaline earth metal salt of a sulphonic acid derived from lignin,
  a polymer containing salified alkylnaphthalenesulphonic acid units,
  a polymer containing vinylsulphonic units or
  a polysaccharide of natural or synthetic, animal or vegetable origin, containing carboxylate, sulphate, sulphonate, or phosphate groups.

5. A composition according to claim 1, in which the wax is selected from the group consisting of beeswax, Chinese wax, carnauba wax, candelilla wax, ouricury wax, cork fibre wax, sugar cane wax, Japan wax, ozokerite, montan wax, a microcrystalline wax and paraffin.

6. A composition according to claim 1, which further comprises a member selected from the group consisting of anionic, non-ionic and amphoteric surface-active agents, in an amount of 3 to 30% by weight.

7. A composition according to claim 1, which also contains a cosmetic ingredient selected from the group consisting of a perfume, preservative, sequestering agent, thickener, softener, non-ionic polymer, oil, silicone, anti-sunburn product and acidifying or alkalising agent.

8. A composition according to claim 1, which is in the form of an anhydrous solid or paste or of an oil-in-water or water-in-oil emulsion.

9. A composition according to claim 1, which is in the form of a mascara, rouge, eye shadow, lipstick or cream for firming the skin.

10. A mascara composition according to claim 9 in which said cationic polymer is a cellulose ether derivative containing quaternary ammonium groups, and said anionic polymer is a sodium polymethacrylate, said composition further comprising, a pigment and a thickener.

11. In a wax based cosmetic composition containing a polymer and from about 2 to 40% by weight of a wax selected from the group consisting of vegetable, animal, mineral and synthetic wax, said wax having a melting point of 60 to 110 degrees C., and a needle penetration according to ASTM Method D5 at 25 degrees C. of 3 to 40 and said wax being solid and rigid at a temperature below 50 degrees C., wherein the improvement comprises said polymer being the combination of a cationic polymer and an amphoteric polymer, said cationic polymer being present in the cosmetic composition in an amount of about 0.1 to 10% by weight and having a molecular weight of 1,000 to 3,000,000, said cationic polymer being a polymer of the polyamine, polyaminopolyamide or poly-(quaternary ammonium) type, the amine or ammonium group forming a part of or being joined to the polymer chain, said amphoteric polymer being present in the cosmetic composition in an amount of about 0.1 to 10% by weight.

12. A composition according to claim 11 in which the amphoteric polymer consists of units A and B randomly distributed in the polymer chain, where A denotes a unit derived form a monomer containing a basic nitrogen atom and B denotes a unit derived from an acid monomer containing a carboxylic or sulphonic acid group, or A and B denote groups derived from zwitterionic carboxybetaine monomers; or A and B denote a cationic polymer chain containing secondary, tertiary or quaternary amine groups, in which one of the amine groups carries a carboxylic or sulphonic acid group joined via a hydrocarbon radical, or A and B form part of a chain of a polymer with an $\alpha,\beta$-dicarboxyethylene unit, in which one of the carboxyl groups has been reacted with a polyamine containing a primary or secondary amine group.

13. In a wax based cosmetic composition containing a polymer and from about 2 to 40% by weight of a wax selected from the group consisting of vegetable, animal, mineral and synthetic wax, said wax having a melting point of 60 to 110 degrees C., and a needle penetration according to ASTM Method D5 at 25 degrees C. of 3 to 40 and said wax being solid and rigid at a temperature below 50 degrees C., wherein the improvement comprises said polymer being the combination of an anionic polymer and an amphoteric polymer, said anionic polymer being present in the cosmetic composition in an amount of about 0.1 to 10% by weight and having a molecular weight of 500 to 3,000,000, said anionic polymer containing carboxylic, sulphonic or phosphoric acid groups, said amphoteric polymer being present in the cosmetic composition in an amount of about 0.1 to 10% by weight.

14. A composition according to claim 13 in which the amphoteric polymer consists of units A and B randomly distributed in the polymer chain, where A denotes a unit derived from a monomer containing a basic nitrogen atom and B denotes a unit derived from an acid monomer containing a carboxylic or sulphonic acid group, or A and B denote groups derived from zwitterionic carboxybetaine monomers; or A and B denote a cationic polymer chain containing secondary, tertiary or quaternary amine groups, in which one of the amine groups carries a carboxylic or sulphonic acid group joined via a hydrocarbon radical, or A and B form part of chain of a polymer with an $\alpha, \beta$-dicarboxyethylene unit, in which one of the carboxyl groups has been reacted with a polyamine containing a primary or secondary amine group.

* * * * *